United States Patent
Nakamura (12) United States Patent (10) Patent No.: US 12,256,908 B2
(45) Date of Patent: Mar. 25, 2025

(54) SPERM COLLECTOR DRIVING DEVICE AND SPERM COLLECTION SYSTEM

(71) Applicant: TENGA Co., Ltd., Tokyo (JP)

(72) Inventor: Kengo Nakamura, Tokyo (JP)

(73) Assignee: TENGA CO., LTD., Tokyo (JP)

( * ) Notice: Subject to any disclaimer, the term of this patent is extended or adjusted under 35 U.S.C. 154(b) by 873 days.

(21) Appl. No.: 17/303,876

(22) Filed: Jun. 9, 2021

(65) Prior Publication Data

US 2021/0401409 A1    Dec. 30, 2021

(30) Foreign Application Priority Data

Jun. 25, 2020   (JP) .................................. 2020-109508

(51) Int. Cl.
*A61B 10/00*   (2006.01)

(52) U.S. Cl.
CPC ................................ *A61B 10/0058* (2013.01)

(58) Field of Classification Search
CPC .... A61B 10/0058; A61H 19/32; A61H 7/005; A61H 9/0057; A61H 2201/1207; A61H 2201/1238; A61H 2205/087
See application file for complete search history.

(56) References Cited

U.S. PATENT DOCUMENTS

| | | | | |
|---|---|---|---|---|
| 4,189,801 A | * | 2/1980 | Lanusse | A46B 13/04 15/247 |
| 4,203,431 A | * | 5/1980 | Abura | A61H 7/005 601/114 |
| 2018/0021212 A1 | * | 1/2018 | Matsuura | A61H 9/0057 600/38 |

FOREIGN PATENT DOCUMENTS

| | | | | |
|---|---|---|---|---|
| CN | 203782811 U | * | 8/2014 | ............... H02K 1/32 |
| CN | 205493883 U | * | 8/2016 | |
| JP | 2008289673 A | * | 12/2008 | |
| JP | 5911033 B1 | * | 4/2016 | ............... H02K 1/32 |
| JP | 2016-209502 A | | 12/2016 | |
| WO | WO2016/132462 A1 | | 8/2016 | |

* cited by examiner

*Primary Examiner* — May A Abouelela
*Assistant Examiner* — Samuel C Kim
(74) *Attorney, Agent, or Firm* — MASUVALLEY & PARTNERS; Peter Martinez (57) ABSTRACT

To provide a sperm collector driving device 100 that detachably holds a sperm collector 200 and rotates the sperm collector 200 in a state of being held, the sperm collector 200 including a core member 210 that is constituted of an elastic material and has an insertion void 214 for a penis provided therein and a container 202 (a container main unit 204) that is constituted of a hollow member having an opening 204*b* in a base end and having a ventilation hole 204*c* in a front portion, and accommodates the core member 210 in an internal space, the sperm collector driving device 100 including a holding unit 120 that detachably holds the sperm collector 200, and a driving mechanism DM that rotates the sperm collector 200 held by the holding unit 120 about an axis, and introduces a negative pressure into the container 202 via the ventilation hole 204*c*.

4 Claims, 10 Drawing Sheets

FIG.2E  FIG.2A  FIG.2D

B-B' SECTIONAL VIEW

| RELEASE SWITCH | |
|---|---|
| NON-OPERATION (OFF) | OPERATION (ON) |
| CLOSE ELECTROMAGNETIC VALVE (BLOCK ATMOSPHERIC PRESSURE) | RELEASE ELECTROMAGNETIC VALVE (INTRODUCE ATMOSPHERIC PRESSURE) |

FIG.10C

| MANUAL SWITCH | |
|---|---|
| LONG-PRESS (TWO SECONDS) | POWER OFF ↔ POWER ON |
| SHORT-PRESS (LESS THAN TWO SECONDS) | ROTATION SPEED KEEP ↔ VARIABLE |

FIG.10D

| GYRO SENSOR | | | |
|---|---|---|---|
| | DRIVING DEVICE | | SPERM COLLECTOR |
| INCLINATION DIRECTION | LEFT ↔ RIGHT | ROTATING DIRECTION | LEFT ↔ RIGHT |
| INCLINATION ANGLE | REFERENCE RANGE ↔ LARGE | ROTATION SPEED | STOP ↔ HIGH |

SPERM COLLECTOR DRIVING DEVICE AND SPERM COLLECTION SYSTEM

CROSS-REFERENCE TO RELATED APPLICATION

This application is based upon and claims the benefit of priorities of the prior Japanese Patent Application No. 2020-109508, filed on Jun. 25, 2020, the entire contents of which are incorporated herein by reference.

FIELD

The present invention relates to a sperm collector driving device and a sperm collection system that can increase efficiency of sperm collection by a sperm collector for collecting sperms from a male.

BACKGROUND

According to the medical demands such as studies and treatment, as well as the social demands such as prevention of sex crimes, prevention of prostitution, and prevention of spreading of sexually transmitted diseases, there have been known sperm collectors (ejaculation facilitating devices for facilitating ejaculation) for collecting sperms from a male.

For example, a sperm collector is used according to the medical demands such as examining the sexual function of a husband based on collected sperms in order to find out the cause of infertility between a husband and a wife, treating sexual dysfunctions, and obtaining and storing sperms for artificial insemination. Further, the sperm collector is used according to various social demands such as prevention of sex crimes, prevention of prostitution, and reduction of the number of people infected with sexually transmitted diseases by solving a personal sexual desire.

As one type of sperm collectors, there have been conventionally known simple sperm collectors that are inexpensively available, and are of disposable type or washable type, thereby causing no hygiene or health issues.

For example, Japanese Patent Application Laid-open No. 2016-209502 discloses a rotary driving device of a sperm receiver including an attachment part for inserting a cylindrical sperm receiver to which a penis can be inserted, an attaching part of the sperm receiver having an air bag to be inserted in a gap between the attachment part and the sperm receiver to fill the gap, and a driving device that rotationally drives the attachment part.

International Publication No. WO2016/132462 discloses a sperm collector including a core member that is produced with a cylindrical elastic material and provided with an insertion void in which a penis inserted in an insertion hole moves relatively, and a container having a base end with an opening, a front end provided with a ventilation hole, and an internal space that accommodates the core member, where a base end portion of the core member is supported in the opening of the container. Further, International Publication No. WO2016/132462 discloses a pressure reducing device that holds a portion on a front end side of the sperm collector, and is capable of decompressing inside the container of the sperm collector through the ventilation hole.

The rotary driving device according to Japanese Patent Application Laid-open No. 2016-209502 electrically rotates and turns the sperm receiver or the like to which a penis is inserted to slide and rub the penis in a rotating direction to give stimulations, thereby facilitating ejaculation.

The pressure reducing device according to International Publication No. WO2016/132462 decompresses the inside of the container of the sperm collector through the ventilation hole to increase stimulations when a penis relatively moving in the insertion void of the core member is slid and rubbed, thereby facilitating ejaculation.

However, although the rotary driving device according to Japanese Patent Application Laid-open No. 2016-209502 can rotate and turn the sperm receiver or the like, it is not capable of decompressing the inside of the sperm collector. Conversely, while the pressure reducing device according to International Publication No. WO2016/132462 can decompress the inside of the sperm collector, it is not capable of rotating the sperm collector.

If the sperm collector can be rotated with the inside of the container being decompressed, as compared to a case where the sperm collector is rotated without decompressing the inside of the container, the stimulations to be given to a penis when the penis is slid and rubbed in the rotating direction increase, so that sperms can be collected efficiently. However, means having a function of rotating the sperm collector while decompressing it has not been proposed.

If the configuration of rotating the sperm collector described in Japanese Patent Application Laid-open No. 2016-209502 is simply combined with the configuration of decompressing the inside of the container of the sperm collector described in International Publication No. WO2016/132462, it is not easy to incorporate evacuating means for decompressing a portion between the two parts that rotate relatively, without hindering the relative rotation between these parts.

The present invention has been achieved in view of such circumstances, and an object of the invention is to collect sperms efficiently.

SUMMARY OF THE INVENTION

In order to solve the above problems, the present invention provides a sperm collector driving device that detachably holds a sperm collector and rotates the sperm collector in a state of being held, the sperm collector including a core member that is constituted of an elastic material and has an insertion void for a penis provided therein and a container that is constituted of a hollow member having an opening in one end in an axial direction and having a ventilation hole in an other part in the axial direction, and accommodates the core member in an internal space, the sperm collector driving device comprising: a holding unit that detachably holds the sperm collector; and a negative-pressure introduction-rotation unit that rotates the sperm collector held by the holding unit about an axis, and introduces a negative pressure into the container via the ventilation hole.

According to the present invention, sperms can be collected efficiently.

DESCRIPTION OF EMBODIMENTS

The present invention will be described below with an embodiment that is illustrated in the drawings. In the following descriptions, a sperm collector driving device 100 is referred to as "driving device 100".

Figure 1A:
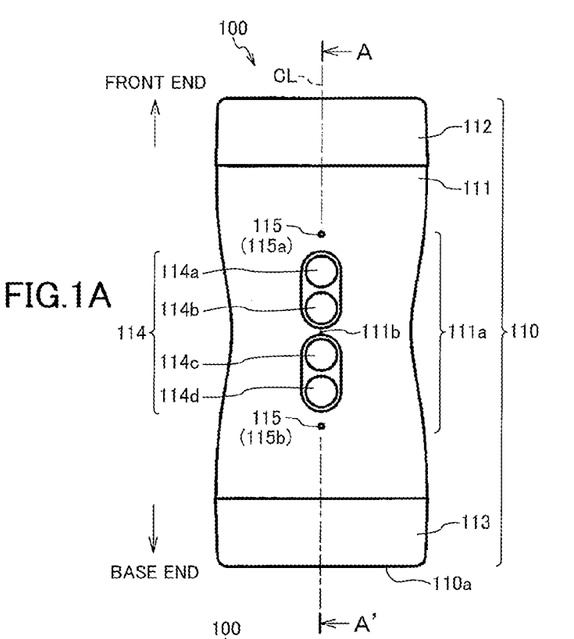
FIGS. 1A to 1D are respectively a front view, a plan view, a bottom view, and a rear view illustrating an external configuration of a sperm collector driving device according to one embodiment of the present invention.
Figure 1B:
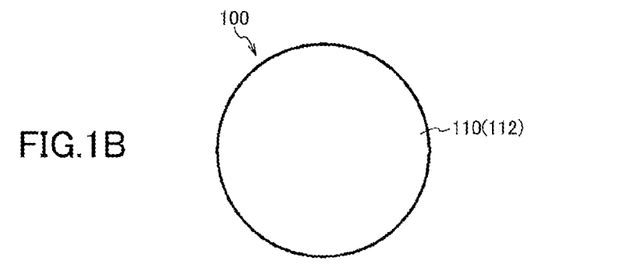
Figure 1C:
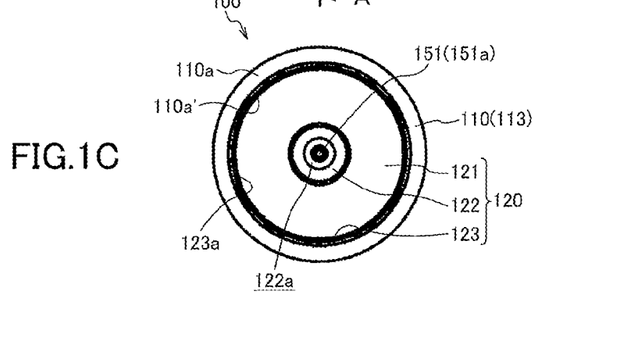
Figure 1D:
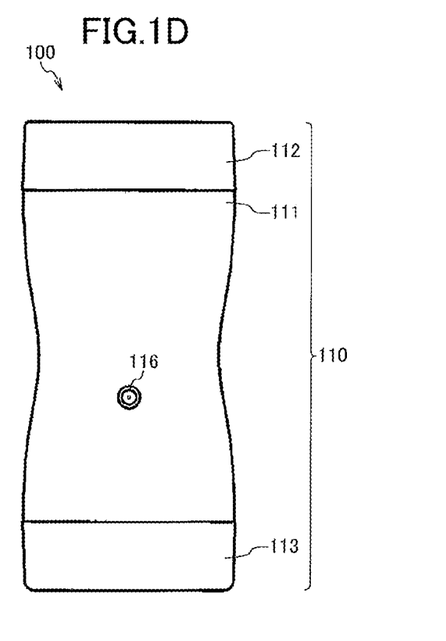
Figure 2A:
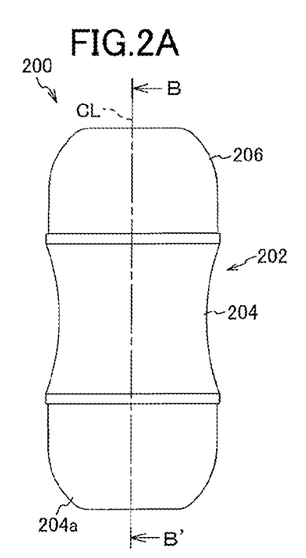
FIGS. 2A to 2E are respectively a front view, a top view, a bottom view, a perspective view, and a B-B' sectional view illustrating a configuration of an example of a sperm collector held in the sperm collector driving device.
Figure 2B:
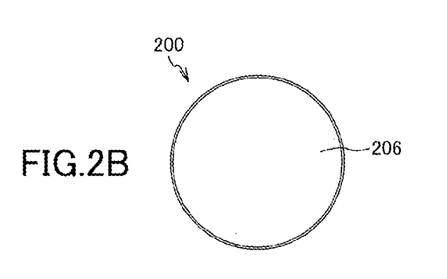
Figure 2C:
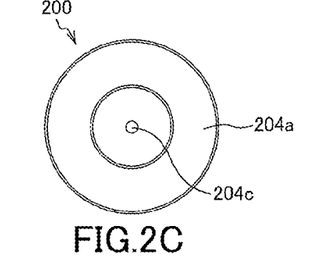
Figure 2D:
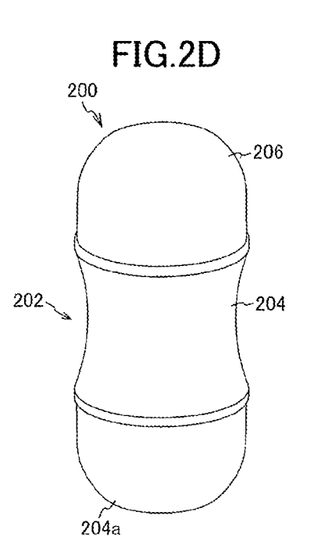
Figure 2E:
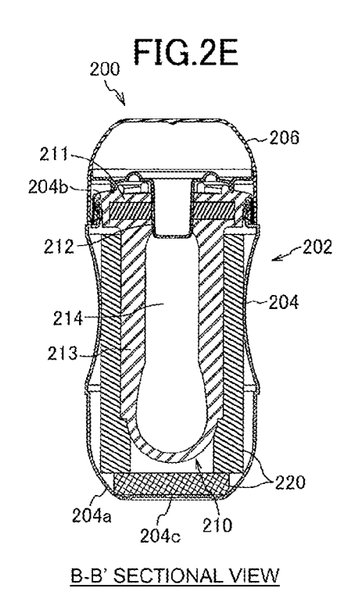
Figure 3:
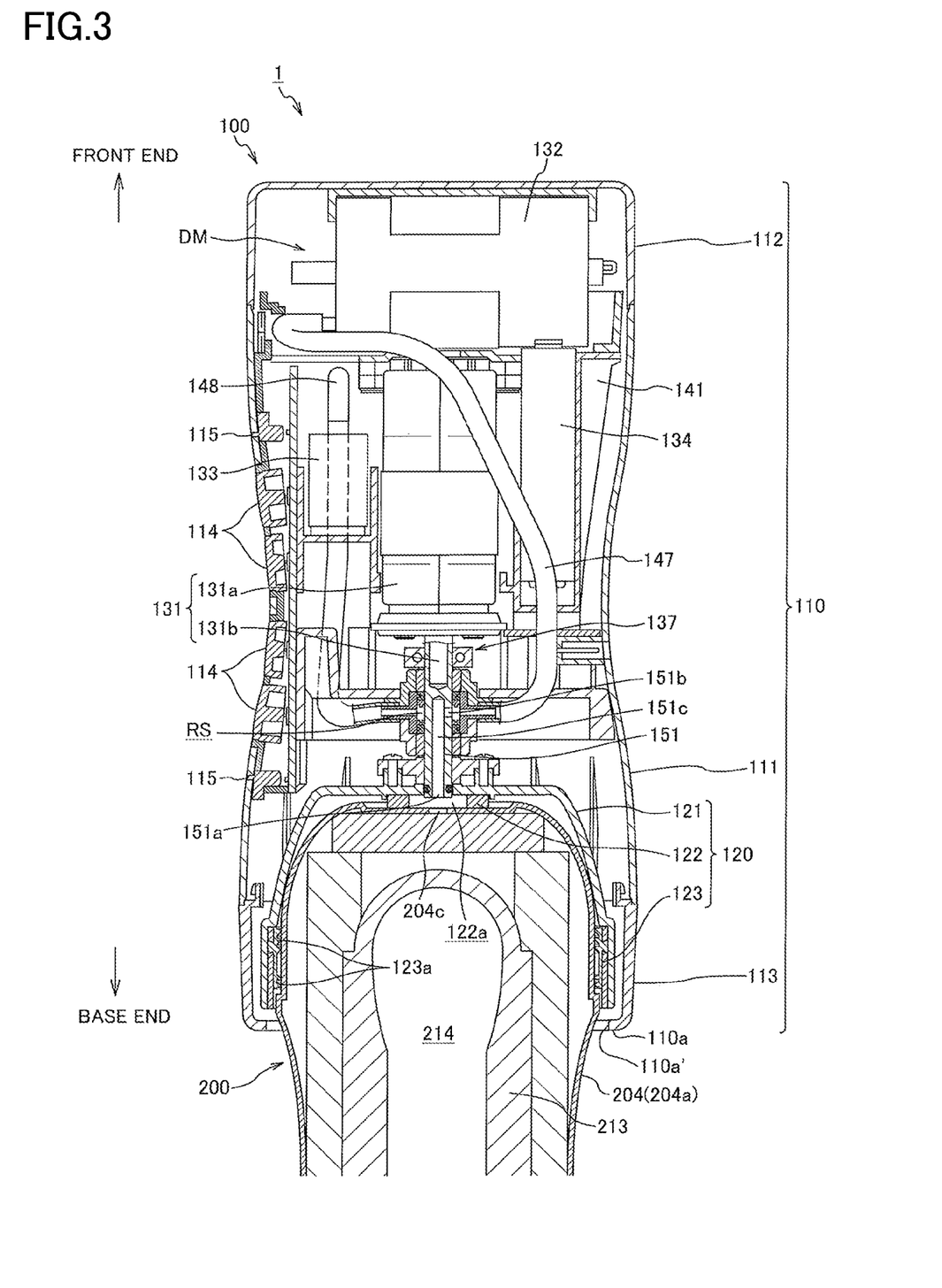
FIG. 3 is an A-A' sectional view of the sperm collector driving device holding a front portion of the sperm collector.

FIGS. 1A to 1D are respectively a front view, a plan view, a bottom view, and a rear view illustrating an external configuration of the driving device 100 according to one embodiment of the present invention, FIGS. 2A to 2E are respectively a front view, a top view, a bottom view, a perspective view, and a B-B' sectional view illustrating a configuration of an example of a sperm collector 200 held in the driving device 100, and FIG. 3 is an A-A' sectional view of the driving device 100 holding a front portion 204a of the sperm collector 200.

The driving device 100 illustrated in FIGS. 1A to 1D is means for efficiently collecting sperms by detachably holding the front portion 204a of the sperm collector 200 exemplified in FIGS. 2A to 2E, rotating the held sperm collector 200 about a center axis CL, and introducing a negative pressure into the sperm collector 200 (into a container). As illustrated in FIG. 3, a sperm collection system 1 is configured by holding the front portion 204a of the sperm collector 200 by the driving device 100.

<Sperm Collector 200>

Prior to descriptions of the driving device 100, the sperm collector 200 is described. As illustrated in FIG. 2A to FIG. 2E, the sperm collector 200 includes a cylindrical core member 210 that is formed of an elastic material such as elastomer and has an insertion hole 212 for a penis provided therein and an insertion void 214 extending from the insertion hole 212, a container 202 constituted of a hollow member made of rigid plastic and accommodating the core member 210 in an internal space, and a cushion member 220 that is arranged between the core member 210 and the container 202 and is produced with an elastic member (a sponge or the like) having air permeability.

The container 202 includes a container main unit 204 including an opening 204b in a base end (one end in an axial direction) and a ventilation hole 204c in the front portion (the other part in the axial direction) 204a, and a cap 206 that is attached to or detached from the opening 204b of the container main unit 204. The core member 210 includes a flange portion 211 having the insertion hole 212 for a penis provided therein, and a cylindrical core main unit 213 having the insertion void 214 for a penis extending from the insertion hole 212 provided therein. The flange portion 211 is fixedly or detachably supported on the opening 204b of the container main unit 204, and the core main unit 213 is supported in the internal space of the container 202 by the cushion member 220 arranged in a periphery thereof. When the cap 206 is attached to the container main unit 204, the flange portion 211 (the insertion hole 212) is covered by the cap 206 and is not visually recognized from outside.

<Outline of Driving Device 100>

Next, an outline of the driving device 100 is described. The driving device 100 illustrated in FIG. 1A to FIG. 1D and FIG. 3 includes a substantially cylindrical casing 110 that can be held by a human hand has an opening 110a' at a base end 110a, a holding unit 120 that is incorporated rotatably (and non-detachably) in the base end opening 110a' of the casing 110 and detachably holds the front portion 204a of the sperm collector 200, and a driving mechanism (negative-pressure introducing rotation unit) DM that rotates the sperm collector 200 accommodated in the casing 110 and held by the holding unit 120 about an axis and introduces a negative pressure into the container 202 through the ventilation hole 204c of the sperm collector 200.

The casing 110 is formed of relatively rigid plastic, and has a constricted portion 111a in an axial intermediate portion. In the constricted portion 111a on a front of the casing 110, four circular switches 114 (114a to 114d) that are operated when the driving device 100 is in use are arranged at intervals in the axial direction. The respective circular switches 114 is described later. On a rear side of the constricted portion 111a, a power supply terminal (female terminal) 116 is provided in which a power plug 149 (see FIG. 7) that supplies power is detachably fitted.

The holding unit 120 is produced with rigid plastic and includes a cup-shaped rotation holder 121 having a recessed inner surface matching with the front portion 204a of the sperm collector 200, a holder-side packing 122 made of an elastic member (for example, rubber or elastic resin) having a ring shape and is attached to a central portion of the inner surface of the rotation holder 121, and a substantially cylindrical locking ring 123 that is produced with rigid plastic and attached to a position near a base end portion of an inner peripheral surface of the rotation holder 121, and has a protrusion 123a formed on the inner peripheral surface to lock the front portion 204a of the sperm collector 200.

As illustrated in FIG. 3, when the front portion 204a of the sperm collector 200 is accommodated in the recessed inner surface of the rotation holder 121, the locking ring 123 locks the front portion 204a of the sperm collector 200. Thus, inside the rotation holder 121, the front portion 204a of the sperm collector 200 is held detachably in a state of being rotatable about the axis with the rotation holder 121.

The holder-side packing 122 is attached on an inner surface of a front end side of the rotation holder 121, and when the rotation holder 121 holds the front portion 204a of the sperm collector 200, it is arranged in a state that the ventilation hole 204c of the sperm collector 200 communicates with an inner peripheral-side void 122a of the holder-side packing 122 and is air tight from outside.

As illustrated in FIG. 3, in an internal space of the casing 110, the driving mechanism (negative-pressure introduction-rotation unit) DM is accommodated that rotates the sperm collector 200 held in the rotation holder 121 about an axis and introduces a negative pressure into the container 202 through the ventilation hole 204c.

The driving mechanism DM includes a motor 131 fixed to a central portion in the casing 110, a pump 132 that is fixed to a front end side of the motor 131 and generates a negative pressure, a shaft 151 that is fixed to each of a rotation shaft 131b of the motor 131 and the rotation holder 121 and rotated about the axis, and is a tubular body communicating between a base end opening 151a (one end opening) and an outer peripheral-surface opening 151b by an in-shaft channel 151c, and a bearing unit 137 that rotatably supports the shaft 151 and forms a pressure regulating space RS around the outer peripheral-surface opening 151b.

The pump 132 and the bearing unit 137 are connected by a pump tube 147, and the negative pressure generated by the pump 132 is introduced into the pressure regulating space RS.

The base end opening 151a of the shaft 151 communicates with the inner peripheral-side void 122a of the holder-side packing 122. Thus, the inner peripheral-side void 122a of the holder-side packing 122 and the pressure regulating space RS of the bearing unit 137 are communicated by the in-shaft channel 151c.

Therefore, when the rotation holder 121 holds the front portion 204a of the sperm collector 200, the negative pressure generated by the pump 132 is introduced into the container 202 of the sperm collector 200 via the pressure regulating space RS of the bearing unit 137, the in-shaft channel 151c, the inner peripheral-side void 122a of the holder-side packing 122, and the ventilation hole 204c of the sperm collector 200. As a result, as compared to a case where the negative pressure is not introduced into the container 202, the degree of close contact between a penis and the core member 210 (an inner surface of the core main unit 213) increases, stimulations given to the penis when the penis is slid and rubbed in the rotating direction by the core member 210 increase, and sperms can be collected efficiently.

Further, the driving mechanism DM is fixed to a left side of the motor 131, and includes an electromagnetic valve 133 connected via the pressure regulating space RS of the bearing unit 137 and a valve tube 148. The electromagnetic valve 133 communicates or blocks between a channel in the valve tube 148 and the internal space of the casing 110. The internal space of the casing 110 is under an atmospheric pressure, and thus when the electromagnetic valve 133 is released while the pump 132 is in operation, each of the negative pressure generated by the pump 132 and the atmospheric pressure is introduced into the pressure regulating space RS of the bearing unit 137. As a result, as compared to a case where the electromagnetic valve 133 is closed and the pump 132 is operated, the negative pressure introduced into the container 202 of the sperm collector 200 decreases, thereby lowering the degree of close contact between the penis and the core member 210, and decreases the stimulations given to the penis.

Figure 4A:
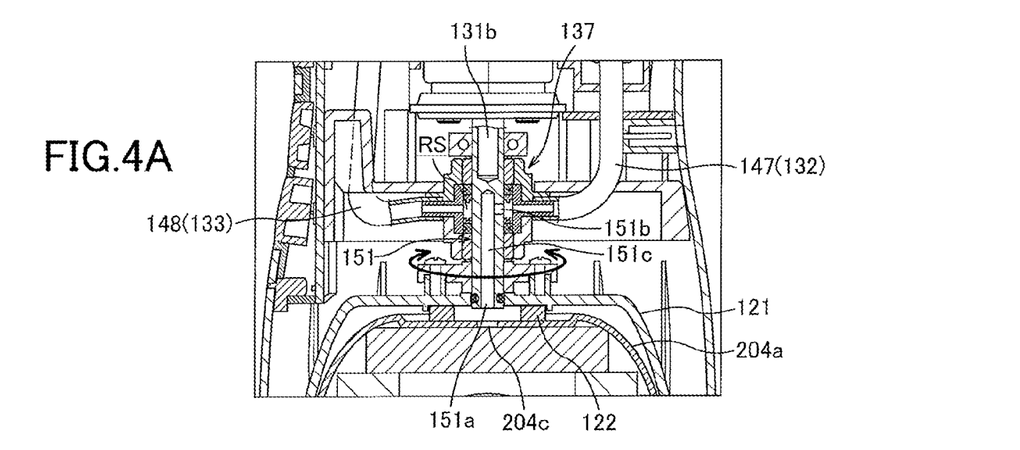
FIG. 4A is an enlarged sectional view of relevant parts when a motor is rotated without operating a pump.
Figure 4B:
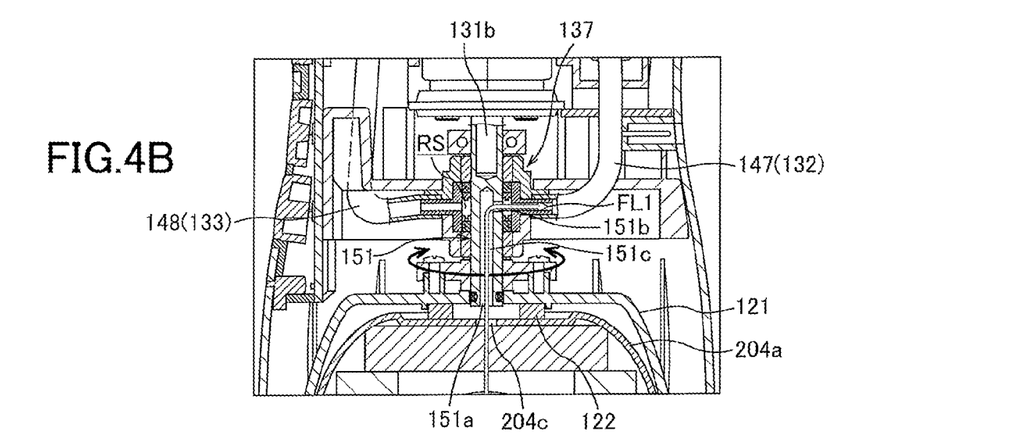
FIG. 4B is an enlarged sectional view of relevant parts when the pump is operated and the motor is rotated.
Figure 4C:
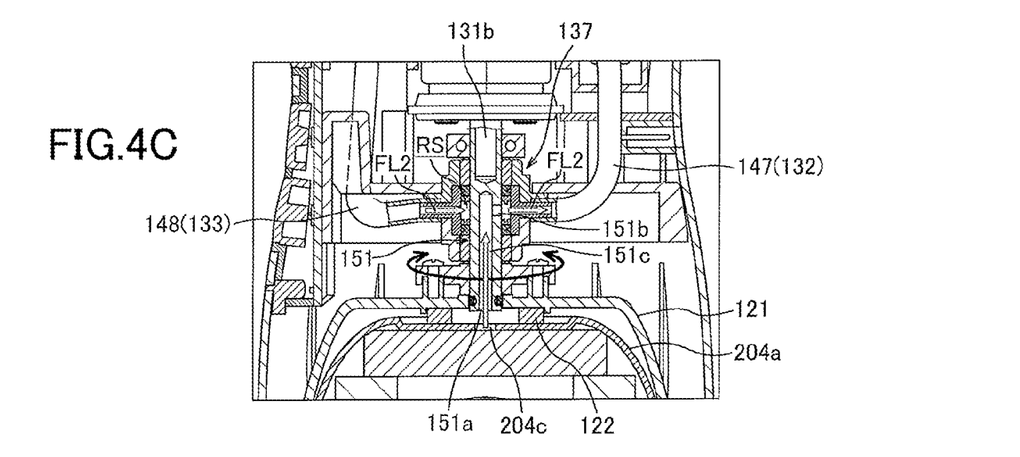
FIG. 4C is an enlarged sectional view when the pump and an electromagnetic valve are operated, and the motor is rotated.

FIG. 4A is an enlarged sectional view of relevant parts when the motor 131 is rotated without operating the pump 132, FIG. 4B is an enlarged sectional view of relevant parts when the pump 132 is operated and the motor 131 is rotated, and FIG. 4C is an enlarged sectional view when the pump 132 and the electromagnetic valve 133 are operated, and the motor 131 is rotated.

As illustrated in FIG. 4A, when the motor 131 is rotated without operating the pump 132, the rotation holder 121 and the sperm collector 200 held by the rotation holder 121 rotate about the axis without having the negative pressure introduced into the container 202 of the sperm collector 200. Therefore, the inside of the container 202 of the sperm collector 200 is at a normal pressure (an atmospheric pressure), and stimulations in the rotating direction are given to the penis inserted in the insertion void 214 of the core member 210.

As illustrated in FIG. 4B, when the motor 131 is rotated while the pump 132 is operated, a flow of air indicated by an arrow with a sign FL1 is generated, and the rotation holder 121 and the sperm collector 200 held by the rotation holder 121 rotate about the axis in a state that the negative pressure is introduced into the container 202 of the sperm collector 200. Therefore, as compared to a case where the motor 131 is rotated without operating the pump 132, the degree of close contact between the penis and the core member 210 increases, and thus the stimulations given to the penis can be increased.

As illustrated in FIG. 4C, when the motor 131 is rotated while the pump 132 and the electromagnetic valve 133 are operated, as indicated by an arrow of a sign FL2, the atmospheric pressure is introduced into the pressure regulating space RS of the bearing unit 137 due to release of the electromagnetic valve 133. Thus, as compared to a case where the pump 132 is operated in a state that the electromagnetic valve 133 is closed, the degree of close contact between the penis and the core member 210 decreases, and the stimulations given to the penis can be decreased.

As described above, by using the driving device 100 according to the present embodiment, the sperm collector 200 can be rotated with the container 202 being decompressed. Thus, as compared to a case where the sperm collector 200 is rotated without decompressing the inside of the container 202, the stimulations given to the penis when the penis is slid and rubbed in the rotating direction can be increased, that is, sperms can be collected efficiently.

<Details of Driving Device 100>

Figure 5:
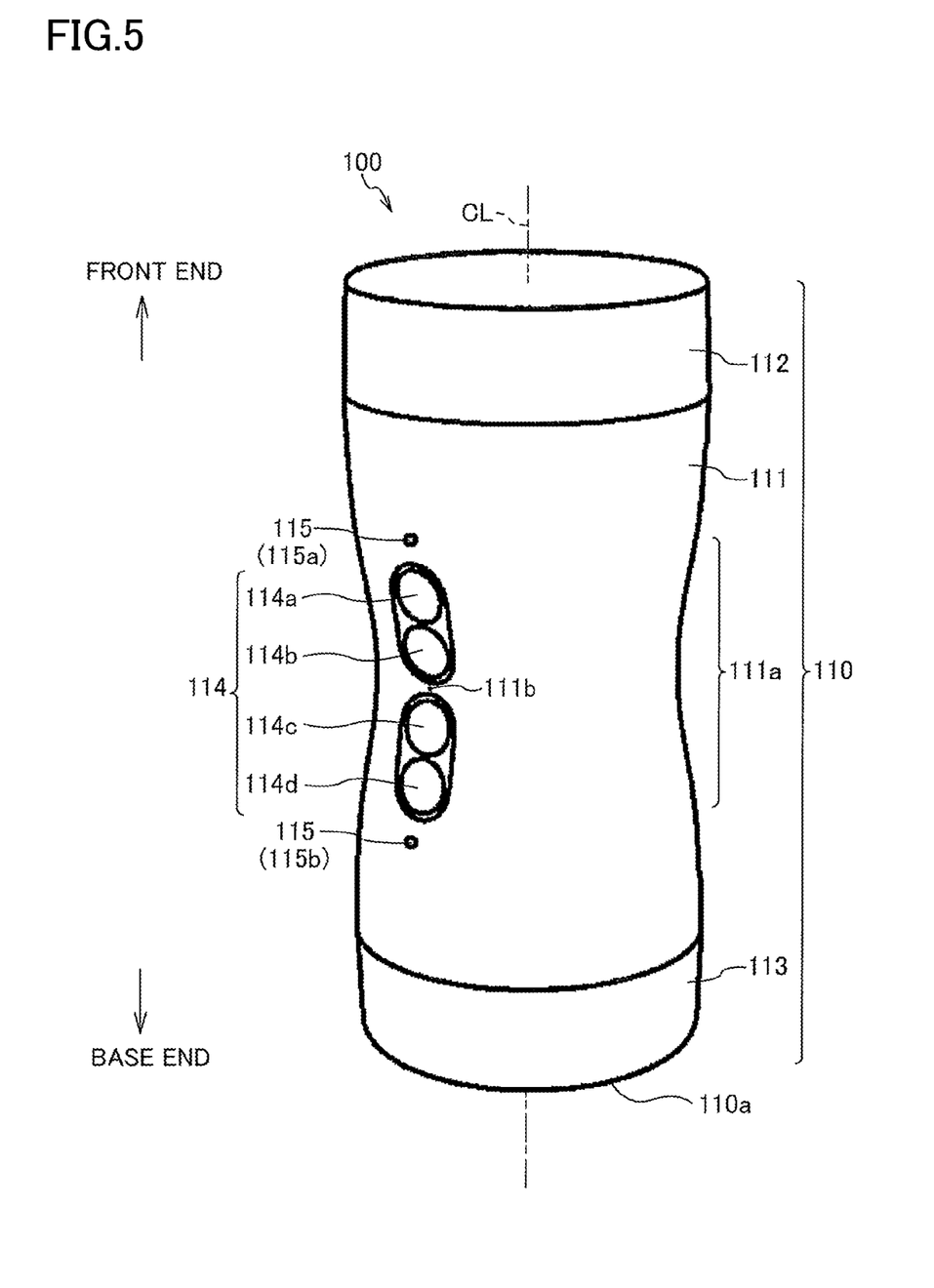
FIG. 5 is a perspective view of the sperm collector driving device.

In the following descriptions, the driving device 100 is described in detail. FIG. 5 is a perspective view of the driving device 100, and FIG. 6 is an exploded perspective view of respective parts constituting the driving device 100.

<Casing 110>

Figure 6:
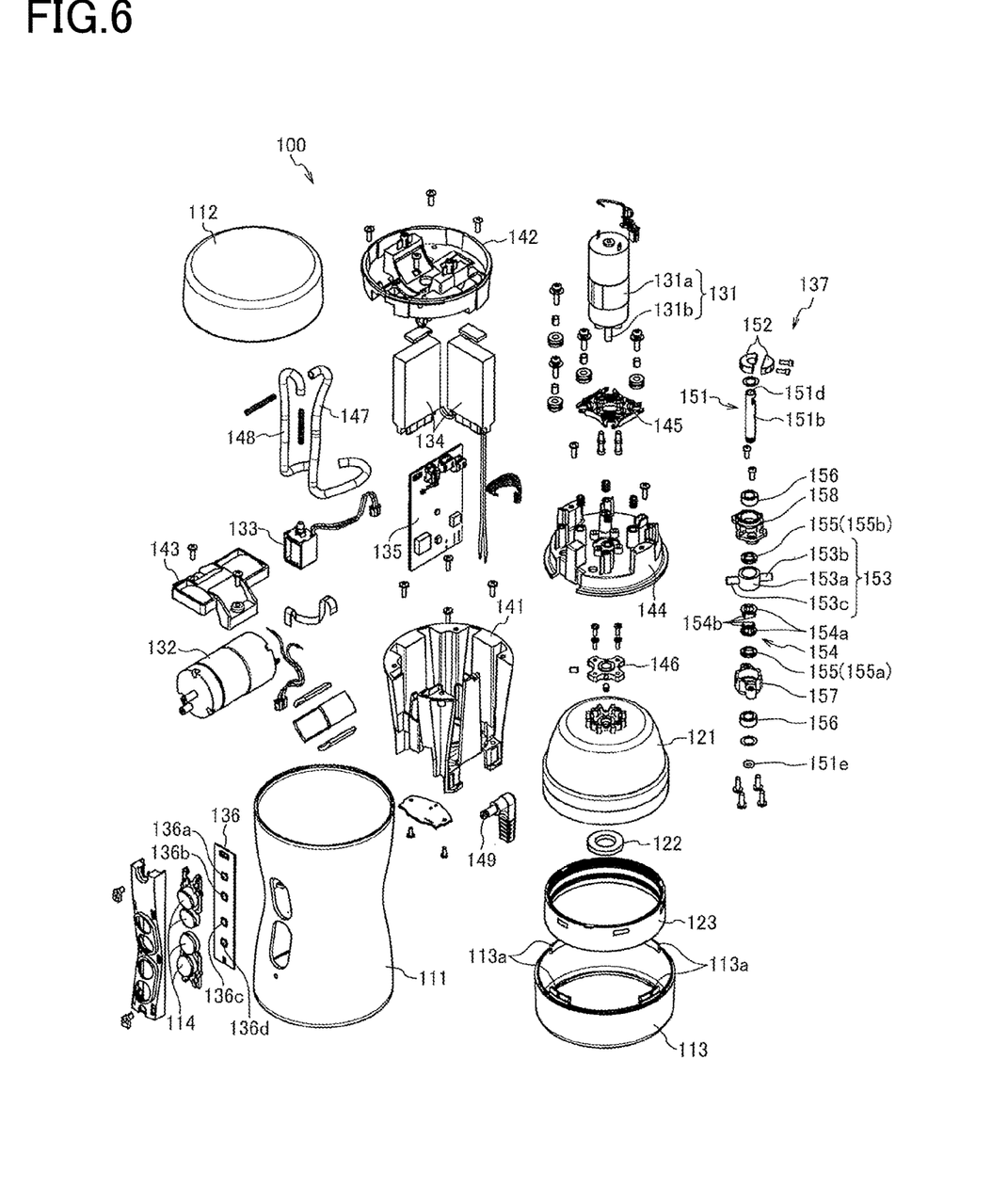
FIG. 6 is an exploded perspective view of respective parts constituting the sperm collector driving device.

As illustrated in FIG. 5 and FIG. 6, the casing 110 includes a substantially cylindrical intermediate case unit 111 having both ends open in the axial direction and the axial intermediate portion (the constricted portion 111a) curved in a recessed shape, a cylindrical base-end case unit 113 that is attached to a base end opening of the intermediate case unit 111 in an aligned state and is penetrated in a vertical direction, and a front-end case unit 112 (lid) that is attached to a front end opening of the intermediate case unit 111 in an aligned state, has a petri-dish shape, and is only open in a base end side, and each of the case units 111, 112, and 113 is made of relatively rigid plastic.

With the base end opening and the front end opening of the intermediate case unit 111, the base-end case unit 113 and the front-end case unit 112 are assembled, respectively, in a state that their peripheral edges are aligned. For example, fixing of the base-end case unit 113 to the intermediate case unit 111 is carried out by engaging a locking projection 113a provided along a peripheral edge of a front end opening of the base-end case unit 113 into a recess (not illustrated) for locking that is provided on the base end opening side of the intermediate case unit 111. The same applies to the fixing structure of the front-end case unit 112 to the intermediate case unit 111.

The constricted portion 111a provided in the casing 110 (the intermediate case unit 111) is a portion to be in contact with the pad of the thumb when the casing 110 is held by a human hand.

As illustrated in FIG. 5, in the constricted portion 111a, the four circular switches 114 (114a to 114d) to be operated when the driving device 100 is in use are arranged at intervals in the axial direction. The two circular switches 114a and 114b are arranged on a front end side of a bottom 111b of the constricted portion 111a, and the two circular switches 114c and 114d are arranged on a base end side of the bottom 111b of the constricted portion 111a.

In the present embodiment, the two circular switches 114a and 114b arranged on the front end side of the bottom 111b of the constricted portion 111a are used when an operation related to introduction of the negative pressure into the sperm collector 200 is performed, and the two circular switches 114c and 114d arranged on the base end side are used when an operation related to rotation of the sperm collector 200 is performed. Specifically, the circular switch 114a arranged at the most front end in the axial direction is a vacuum switch and is operated when turning on the power of the pump 132 or switching a vacuum mode (described later). The circular switch 114b arranged on a base end side of the vacuum circular switch 114a is a release switch (a valve switch), and is operated to release the electromagnetic valve 133 to decrease the stimulations given to the penis while the pump 132 is in operation.

The circular switch 114c arranged on a base end side of the release switch 114b across the bottom 111b of the constricted portion 111a is a manual switch, and is operated when the power to the motor 131 is turned on and off or when the rotation speed of the sperm collector 200 is maintained. The circular switch 114d arranged on a base end side of the manual switch 114c is an automatic switch, and is operated when turning on or off the power to the motor 131 or when switching an automatic mode (described later).

In the casing 110, an illumination display unit 115 (a first illumination display unit 115a) that indicates that the pump 132 is turned on by illumination is provided on a front end side of the vacuum switch 114a, and another illumination display unit 115 (a second illumination display unit 115b) that indicates that the motor 131 is turned on by illumination is provided on a base end side of the automatic switch 114d.

For example, these illumination display units 115a and 115b are produced with a set of an LED 115c and a light guiding member 115d (see FIG. 7), and an illumination color is green for example, but other colors may be employed.

<Internal Configuration of Casing 110>

Figure 7:
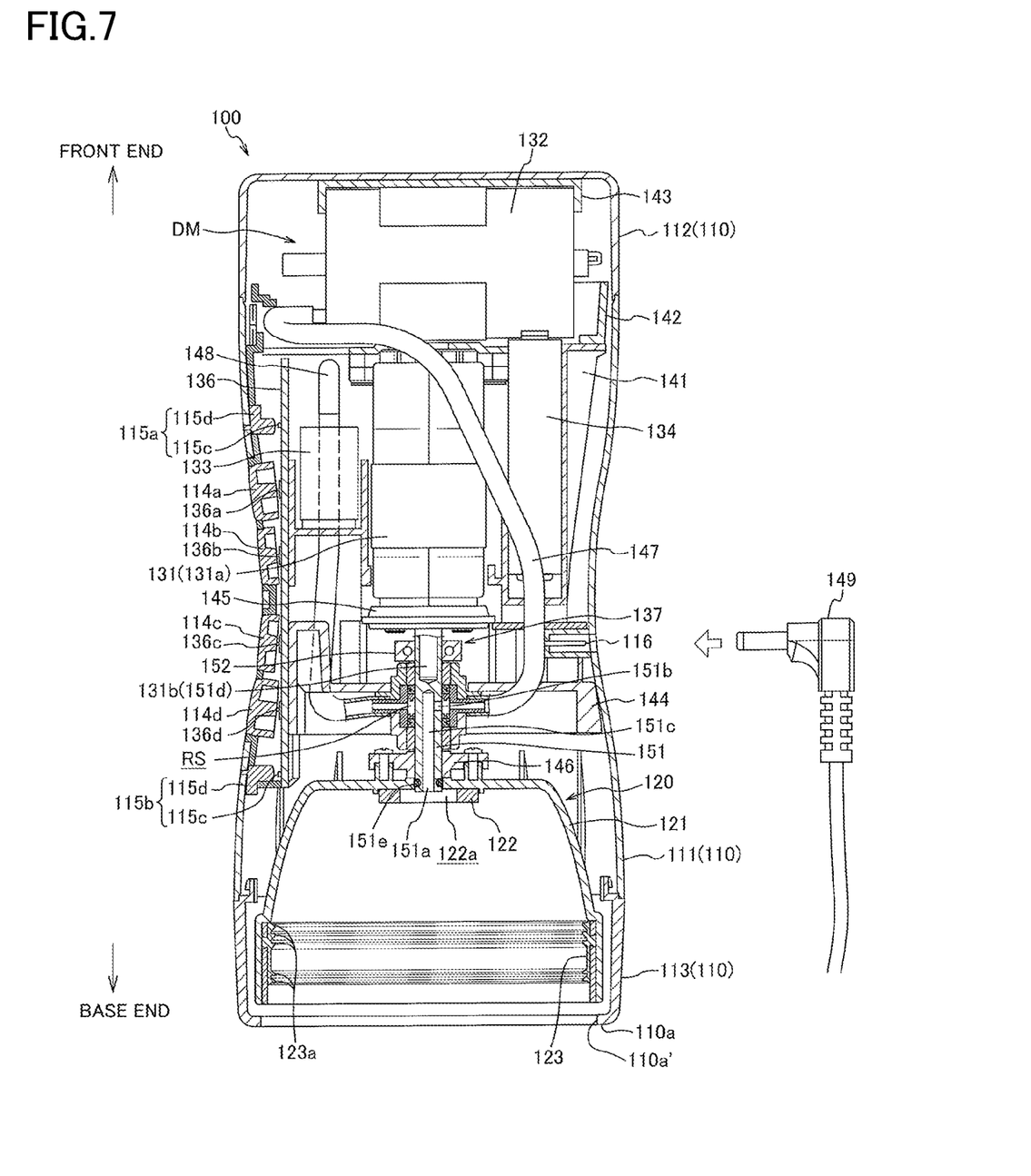
FIG. 7 is a vertical sectional view of the sperm collector driving device.

Next, an internal configuration of the casing 110 is described. FIG. 7 is a vertical sectional view of the driving device 100.

As illustrated in FIG. 7, the driving mechanism DM is accommodated in the internal space of the casing 110, and the holding unit 120 is rotatably (and undetachably) incorporated in the base end opening 110a' of the casing 110.

As described above, the holding unit 120 includes the cup-shaped rotation holder 121 having a recessed inner surface matching with the front portion 204a of the sperm collector 200, the holder-side packing 122 that is attached to the central portion of the inner surface of the rotation holder 121, and the substantially cylindrical locking ring 123 that is attached to the position near the base end portion of the inner peripheral surface of the rotation holder 121. The driving mechanism DM is means for rotating the sperm collector 200 held by the rotation holder 121 about the axis and introducing a negative pressure into the container 202 through the ventilation hole 204c, as described above.

<Driving Mechanism DM>

As illustrated in FIG. 6 and FIG. 7, the driving mechanism DM includes the motor 131 that is fixedly arranged in a central portion in the internal space of the casing 110 with the rotation shaft 131b being directed toward the base end side, the pump 132 that is fixedly arranged on the front end side of the motor 131 and generates a negative pressure, the electromagnetic valve 133 that is fixedly arranged between the motor 131 and the circular switches 114, the shaft 151 that is the tubular body that couples the rotation shaft 131b of the motor 131 and the holding unit 120 (the rotation holder 121) and transmits rotations of the motor 131 to the holding unit 120 and communicates between the base end opening 151a provided on a base end and the outer peripheral-surface opening 151b provided on an outer peripheral surface by the in-shaft channel 151c, and the bearing unit 137 that rotatably supports the shaft 151 and forms the pressure regulating space RS, to which the negative pressure generated by the pump 132 is introduced, around the outer peripheral-surface opening 151b, as main constituent elements.

Other than these elements, the driving mechanism DM includes a battery 134 that is arranged near the motor 131 and supplies power, a main substrate 135 on which a controller 135a (a control unit) and a gyro sensor 135b (see FIG. 9) are mounted and that controls operations of the motor 131, the pump 132, and the electromagnetic valve 133 based on an operation on each of the circular switches 114 or a turning operation on the driving mechanism DM, and a switch substrate 136 on which switch elements 136a to 136d that are provided in a manner corresponding to the respective circular switches 114 (114a to 114d) and that are operated to turn on or off based on an operation on each of the circular switches 114, and a light emitting element such as the LED 115c are mounted.

The motor 131, the electromagnetic valve 133, the battery 134, and the main substrate 135 are attached to an inner-case main unit 141. On a front end of the inner-case main unit 141, an inner-case lid 142 is attached, and the pump 132 is attached to the inner-case lid 142 by a pump holder 143.

The motor 131 includes a motor main unit 131a and the rotation shaft 131b provided to project from a base end of the motor main unit 131a. A base end portion of the motor main unit 131a is fixed to an inner-base member 144 via a motor holder 145. The rotation shaft 131b is fitted in an attachment hole 151d provided in a tip of the shaft 151, fixed with a motor collar 152, and integrally rotates with the shaft 151.

A base end side portion of the shaft 151 is fixed to a front end of the rotation holder 121 via a coupling 146. The base end of the shaft 151 penetrates the front end of the rotation holder 121, and the base end opening 151a faces the inner peripheral-side void 122a of the holder-side packing 122. An O-ring 151e is attached to the base end of the shaft 151, and seals the rotation holder 121 and the shaft 151 in an air-tight state. On an outer peripheral surface in an axial intermediate position of the shaft 151, the outer peripheral-surface opening 151b is formed, and the in-shaft channel 151c communicates between the base end opening 151a and the outer peripheral-surface opening 151b.

On the periphery of the shaft 151, the bearing unit 137 that rotatably supports the shaft 151 and forms the pressure regulating space RS around the outer peripheral-surface opening 151b is provided. Therefore, the in-shaft channel 151c communicates between the pressure regulating space RS of the bearing unit 137 and the inner peripheral-side void 122a of the holder-side packing 122. The bearing unit 137 is described later in detail.

The pressure regulating space RS and the pump 132 are communicated by the pump tube 147. Therefore, the negative pressure generated by the pump 132 is introduced into the pressure regulating space RS via the pump tube 147. Similarly, the pressure regulating space RS and the electromagnetic valve 133 are communicated via the valve tube 148. As described above, the electromagnetic valve 133 is arranged in the internal space (at the atmospheric pressure) of the casing 110, and communicates and blocks between the channel of the valve tube 148 and the internal space of the casing 110. Therefore, when the electromagnetic valve 133 is open, the atmospheric pressure is introduced into the pressure regulating space RS via the valve tube 148.

<Bearing Unit 137>

Figure 8:
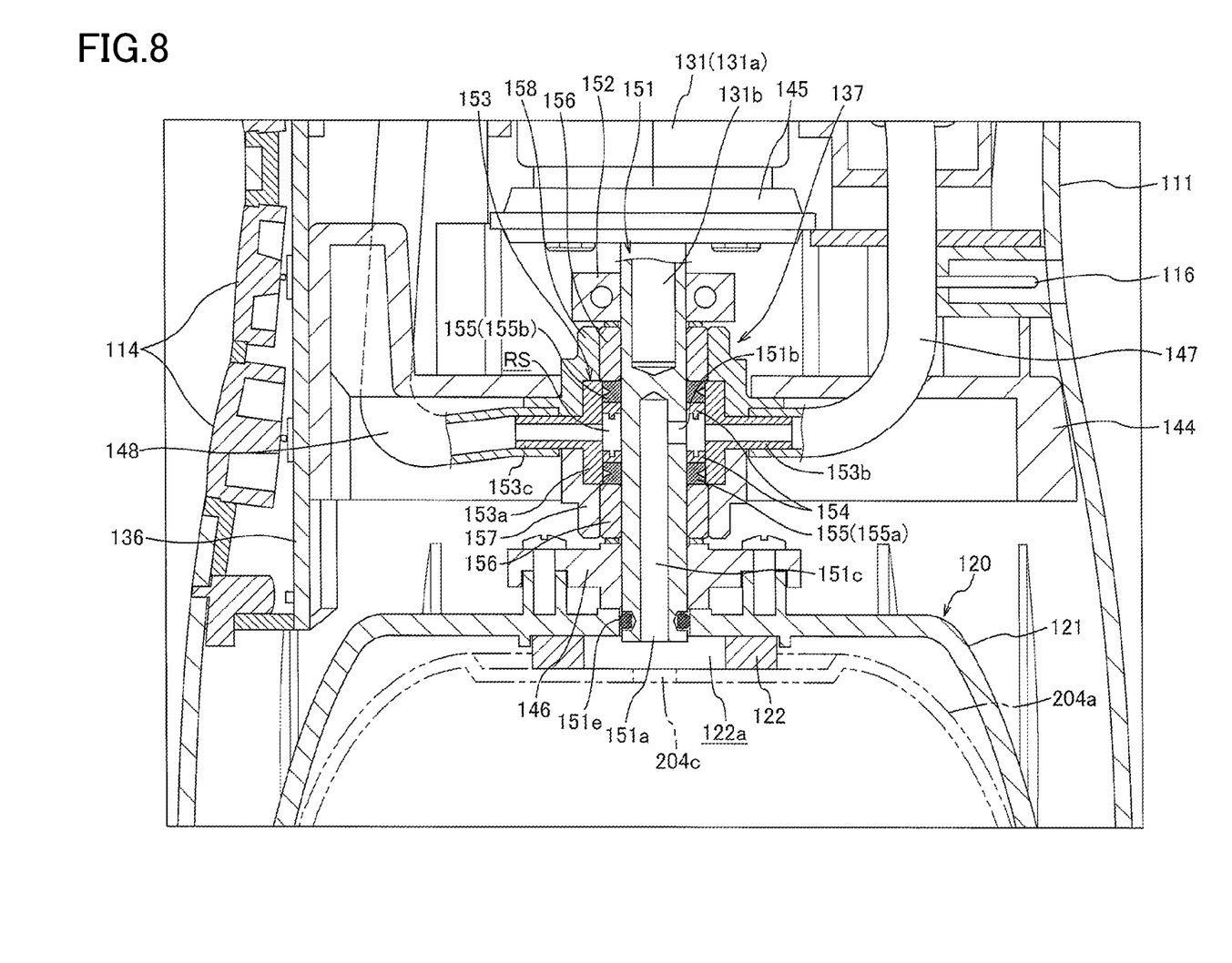
FIG. 8 is a partially-enlarged sectional view of a periphery of a bearing unit of the sperm collector driving device.

FIG. 8 is a partially-enlarged sectional view of a periphery of the bearing unit 137 of the driving device 100.

As illustrated in FIG. 6 and FIG. 8, the bearing unit 137 includes a spacer 153 through which the shaft 151 is inserted, a bearing collar 154 arranged in the spacer 153, a pair of X-rings 155 (155a, 155b) that air-tightly seal a portion between the shaft 151 and the spacer 153 while allowing the shaft 151 to rotate, a pair of bearings 156 that have an inner void in which the shaft 151 is inserted and that are arranged between the X-ring 155a on the base end side and the coupling 146 and between the X-ring 155b on the front end side and the motor collar 152, respectively, a base-end side bearing holder 157 that holds the spacer 153 and the bearing 156 on the base end side from the base end side, and a front-end side bearing holder 158 that holds the spacer 153 and the bearing 156 on the front end side from the front end side.

The spacer 153 includes a cylindrical spacer main unit 153a having both ends open in the axial direction in which the shaft 151 is inserted, and a pair of connecting pipes 153b and 153c that are provided on an outer peripheral surface of the spacer main unit 153a and have an inner channel communicating with an inner void of the spacer main unit 153a, and is produced with rigid plastic, for example.

The spacer main unit 153a has a cylindrical shape having an inner diameter larger than an outer diameter of the shaft 151, but may also be a square cylindrical shape. The connecting pipes 153b and 153c have a cylindrical shape having a diameter smaller than an axial height of the spacer main unit 153a, and include the pump connecting pipe 153b to which an end of the pump tube 147 is connected and the valve connecting pipe 153c to which an end of the valve tube 148 is connected. In the present embodiment, the valve connecting pipe 153c is provided at a position that is turned 180 degrees about the axis from the pump connecting pipe 153b, but is not limited to this angle.

The bearing collar 154 is a member arranged in the inner void of the spacer main unit 153a so that the pair of X-rings 155a and 155b is positioned respectively on the both ends of the spacer main unit 153 in the axial direction, and includes a pair of rings 154a and a leg part 154b for spacing between the pair of rings 154a, for example.

The X-ring 155 (155a, 155b) is a ring body having a X-shaped cross section, and is produced with an elastic material having airtightness, such as rubber for example. The X-ring 155 includes the base-end side X-ring 155a (one-end side packing) attached to the base-end opening 151a of the spacer main unit 153a and the front-end side X-ring 155b (the other-end side packing) attached to a front end opening of the spacer main unit 153a.

In the present embodiment, because the bearing collar 154 is arranged in the internal space of the spacer main unit 153a, the base-end side X-ring 155a and the front-end side X-ring 155b can be arranged at an interval in the axial direction. Thus, a disadvantage that the respective X-rings 155a and 155b block the internal channels of the respective connecting pipes 153b and 153c is prevented.

The bearings 156 are members that rotatably and axially support the shaft 151, and are held by the base-end side bearing holder 157 and the front-end side bearing holder 158, respectively.

The pressure regulating space RS is formed by the spacer main unit 153a, the base-end side X-ring 155a, and the front-end side X-ring 155b. The outer peripheral-surface opening 151b of the shaft 151 is positioned in the pressure regulating space RS even when the shaft 151 rotates, and thus the pressure regulating space RS and the inner peripheral-side void 122a of the holder-side packing 122 communicate through the outer peripheral-surface opening 151b, the in-shaft channel 151c, and the base end opening 151a when the shaft 151 rotates.

As described above, the pump tube 147 is connected to the pump connecting pipe 153b, and the negative pressure generated by the pump 132 is introduced into the pressure regulating space RS. Similarly, the valve tube 148 is connected to the valve connecting pipe 153c, and the atmospheric pressure is introduced into the pressure regulating space RS when the electromagnetic valve 133 is released.

When the front portion 204a of the sperm collector 200 is held by the holding unit 120 (the rotation holder 121), the base end opening 151a of the shaft 151 and the ventilation hole 204c of the sperm collector 200 communicate with each other in an air-tight state from outside. Therefore, by operating the pump 132, the negative pressure generated by the pump 132 can be introduced into the container 202 of the sperm collector 200. Thus, as compared to a case where the negative pressure is not introduced into the container 202 of the sperm collector 200, the stimulations given to a penis can be increased. Similarly, when the electromagnetic valve 133 is released while the pump 132 is in operation, the degree of close contact between the penis and the core member 210 decreases as compared to a case where the pump 132 is operated in a state that the electromagnetic valve 133 is closed.

In this manner, the driving device 100 according to the present embodiment can adjust the stimulations given to a penis by the motor 131, the pump 132, and the electromagnetic valve 133.

<Configuration of Control System>

Figure 9:
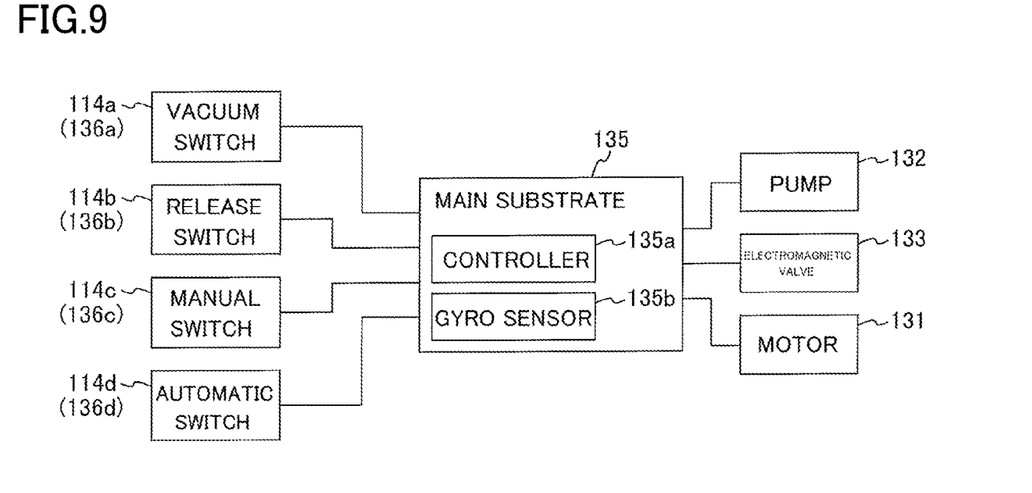
FIG. 9 is a block diagram illustrating a configuration of a control system of the sperm collector driving device.
Figure 10A:
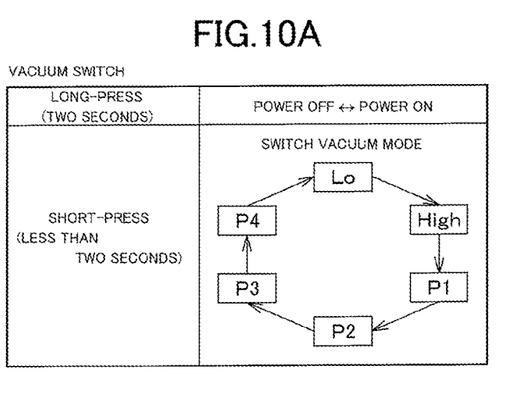
FIG. 10A to FIG. 10E are respectively an explanatory diagram of operations and control contents of a vacuum switch, an explanatory diagram of operations and control contents of a release switch, an explanatory diagram of operations and control contents of a manual switch, an explanatory diagram of operations on the sperm collector driving device based on a detection signal of a gyro sensor and control contents of the sperm collector, and an explanatory diagram of operations and control contents of an automatic switch.
Figure 10B:
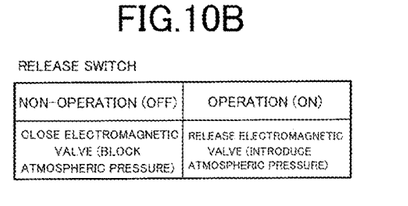
Figure 10C:
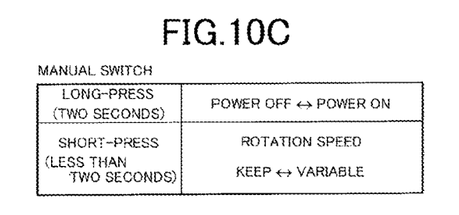
Figure 10D:
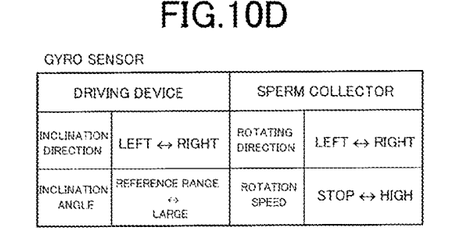
Figure 10E:
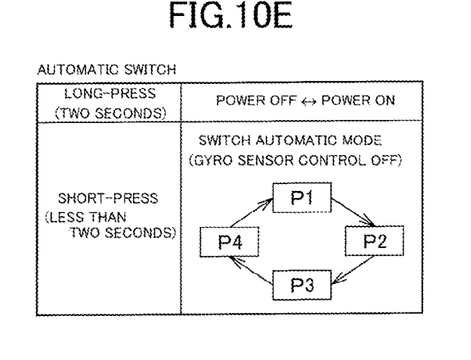
Figure 11:
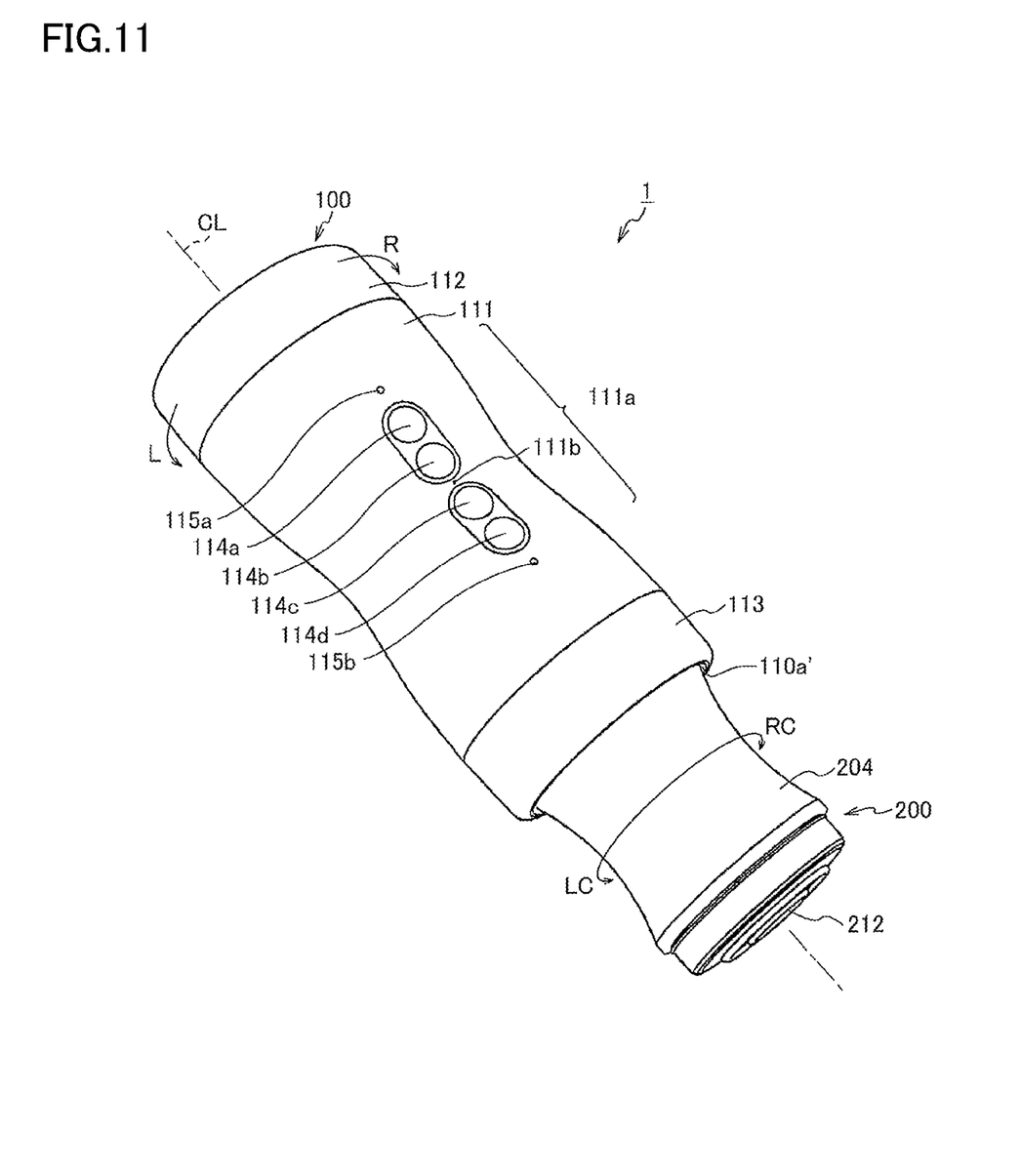
FIG. 11 is a perspective view for explaining a method of using a sperm collection system.

FIG. 9 is a block diagram illustrating a configuration of a control system of the driving device 100, FIG. 10A to FIG. 10E are respectively an explanatory diagram of operations and control contents of the vacuum switch 114a, an explanatory diagram of operations and control contents of the release switch 114b, an explanatory diagram of operations and control contents of the manual switch 114c, an explanatory diagram of operations on the driving device 100 based on a detection signal of the gyro sensor 135b and control contents of the sperm collector 200, an explanatory diagram of operations and control contents of the automatic switch 114d, and FIG. 11 is a perspective view for explaining a method of using the sperm collection system 1.

As illustrated in FIG. 9, the main substrate 135 is provided with the controller 135a as a center of control of the driving device 100, and the gyro sensor 135b (angular velocity sensor) that outputs a detection signal according to an angular velocity when the casing 110 is turned.

Further, the vacuum switch 114a (the switch element 136a), the release switch 114b (the switch element 136b), the manual switch 114c (the switch element 136c), the automatic switch 114d (the switch element 136d), the pump 132, the electromagnetic valve 133, and the motor 131 are electrically connected to the main substrate 135. Further, although illustrations thereof are omitted, the LED 115c is also electrically connected to the main substrate 135.

The controller 135a controls operations of the pump 132, the electromagnetic valve 133, and the motor 131 based on operations on the respective switches 114a to 114d and a detection signal from the gyro sensor 135b. For example, the controller 135a is constituted of any one of a programmable controller, a hardware logic, or a set of a CPU and a memory, or a combination thereof. The gyro sensor 135b detects the angular velocity of the casing 110, and outputs the detection signal to the controller 135a.

In the following descriptions, the relationship between the operations on the respective switches 114a to 114d and the control contents by the controller 135a is described.

<Vacuum Switch 114a>

The vacuum switch 114a is operated when turning on or off the power supply to the pump 132, or when switching an operating mode (hereinafter, "vacuum mode") of the pump 132.

As illustrated in FIG. 10A, when the vacuum switch 114a is long-pressed for two or more seconds, the power supply to the pump 132 can be turned on or off. For example, when the vacuum switch 114a is long-pressed at a time of a power-off state, the controller 135a shifts to a power-on state, thereby allowing the power from the battery 134 to be supplied to the pump 132. Similarly, when the vacuum switch 114a is long-pressed at a time of the power-on state, the controller 135a shifts to the power-off state, thereby stopping the power supply from the battery 134 to the pump 132.

Further, during the power-on state, when the vacuum switch 114a is short-pressed for less than two seconds, the vacuum mode is switched.

For example, the controller 135a sets the vacuum mode to a vacuum mode "Lo" just after the power is turned on. In the vacuum mode "Lo", the pump 132 generates a weak negative pressure, and this negative pressure is introduced into the container 202 of the sperm collector 200.

When the vacuum switch 114a is short-pressed once from the state of the vacuum mode "Lo", the controller 135a switches to a vacuum mode "Hi". In the vacuum mode "Hi", the pump 132 generates a strong negative pressure, and this negative pressure is introduced into the container 202 of the sperm collector 200.

When the vacuum switch 114a is short-pressed once from the state of the vacuum mode "Hi", the controller 135a switches to a vacuum mode "P1". In the vacuum mode "P1", the pump 132 is operated in a predetermined pattern. For example, the pump 132 repeats an operating state and a stopped state at a predetermined first period. Thus, the pump 132 generates a negative pressure repeatedly at the first period, and this negative pressure is introduced into the container 202 of the sperm collector 200.

When the vacuum switch 114a is short-pressed once from the state of the vacuum mode "P1", the controller 135a switches to a vacuum mode "P2". Similarly, the controller 135a switches to a vacuum mode "P3", and to a vacuum mode "P4" every time the vacuum switch 114a is pressed once.

In the vacuum modes "P2" to "P4", the pump 132 is operated in a predetermined pattern. For example, the pump 132 repeats the operating state and the stopped state at a second period that is shorter than the first period in the vacuum mode "P2", repeats the operating state and the stopped state at a third period that is shorter than the second period in the vacuum mode "P3", and repeats the operating state and the stopped state at a fourth period that is shorter than the third period in the vacuum mode "P4".

Thus, the pump 132 repeatedly generates a negative pressure from the second period to the fourth period, and the negative pressure is introduced into the container 202 of the sperm collector 200.

<Release Switch 114b>

The release switch 114b is operated to open the electromagnetic valve 133 while the pump 132 is in operation.

As illustrated in FIG. 10B, the electromagnetic valve 133 is closed in a non-operating state (off state) that the release switch 114b is not operated. As described above, in the closed state of the electromagnetic valve 133, the atmospheric pressure is not introduced into the pressure regulating space RS of the bearing unit 137, and thus the negative pressure generated by the pump 132 is introduced into the container 202 of the sperm collector 200 through the pressure regulating space RS.

In an operating state (on state) that the release switch 114b is operated, the electromagnetic valve 133 is released. As described above, in the released state of the electromagnetic valve 133, the atmospheric pressure is introduced into the pressure regulating space RS of the bearing unit 137, and thus the negative pressure introduced into the container 202 of the sperm collector 200 is decreased as compared to a case where the electromagnetic valve 133 is closed and the pump 132 is operated.

In this manner, by operating the release switch 114b while the pump 132 is in operation, the negative pressure introduced into the container 202 is decreased, and thus the stimulations given to a penis can be adjusted.

In the driving device 100 according to the present embodiment, the release switch 114b is operated when adjusting the stimulations given to a penis, and thus the release switch 114b is assumed to be operated more frequently than the vacuum switch 114a.

For example, the operation of turning on or off the power supply to the pump 132 is performed at a start or end of use of the driving device 100, and once it is determined which vacuum mode to use, the operation of switching the vacuum mode is not performed until the mode is changed. On the other hand, the operation on the release switch 114b is performed when it is desired to increase or decrease the stimulations given to a penis, and thus it is assumed to be used a large number of times while the driving device 100 is in use.

Therefore, the release switch 114b is operated more frequently than the vacuum switch 114a.

As illustrated in FIG. 11, in the present embodiment, the release switch 114b is provided at a location closer to the bottom 111b of the constricted portion 111a than the vacuum switch 114a.

It is assumed that the pad of the thumb when the driving device 100 is held by a human hand is located at the bottom 111b of the constricted portion 111a. Thus, by providing the release switch 114b, which is more frequently used than the vacuum switch 114a, at a location closer to the bottom 111b of the constricted portion 111a than the vacuum switch 114a, the amount of moving the thumb can be reduced when the release switch 114b is operated, and erroneous operations on the vacuum switch 114a can be prevented.

<Manual Switch 114c>

The manual switch 114c is operated when the power supply to the motor 131 is turned on or off, or when the rotation mode of the motor 141 (the sperm collector 200) is changed.

As illustrated in FIG. 10C, when the manual switch 114c is long-pressed for two or more seconds, the power supply to the motor 131 can be turned on or off. For example, when the manual switch 114c is long-pressed at a time of the power-off state, the controller 135a shifts to the power-on state, and allows the power from the battery 134 to be supplied to the motor 131. Similarly, when the manual switch 114c is long-pressed at a time of the power-on state, the controller 135a shifts to the power-off state, and stops the power supply from the battery 134 to the motor 131.

Further, when the manual switch 114c is short-pressed for less than two seconds at a time of the power-on state, the rotation mode is switched.

The rotation mode includes a keeping mode for changing the rotating direction of the sperm collector 200 (the motor 131) corresponding to a turning direction of the driving device 100 (the casing 110) while being kept at a constant rotation speed, and a variable mode for changing the rotating direction and rotation speed of the sperm collector 200 corresponding to the turning direction and the size of a turning angle of the driving device 100.

The controller 135a detects the turning direction and the turning angle of the driving device 100 based on the detection signal of the gyro sensor 135b. For example, the controller 135a obtains the turning angle of the driving device 100 based on the detection signal of the gyro sensor 135 as an initial origin at a time point when the manual switch 114c is long-pressed to shift to the power-on state. When the driving device 100 is turned in one direction (for example, a right direction indicated by a sign R in FIG. 11) or the other direction (for example, a left direction indicated by a sign L in FIG. 11) from the initial origin, the controller 135a obtains the turning direction from the initial origin as an inclination direction, and obtains an angular difference from the initial origin after the turning as an inclination angle (a turning angle).

In the present embodiment, the controller 135a sets the variable mode when the manual switch 114c is long-pressed to turn the power on.

As illustrated in FIG. 10D, in the variable mode, the controller 135a controls the motor 131 to rotate the sperm collector 200 in the right direction when the inclination direction of the driving device 100 is the right direction, or controls the motor 131 to rotate the sperm collector 200 in the left direction when the inclination direction of the driving device 100 is the left direction. Furthermore, the controller 135a stops the rotation of the sperm collector 200 when the inclination angle is within a reference range (for example, in a range of ±5 degrees from the initial origin). When the inclination angle exceeds the reference range, the controller 135a increases the rotation speed of the sperm collector 200 as the inclination angle becomes larger.

The controller 135a shifts to the keeping mode when the manual switch 114c is short-pressed in the variable mode, and keeps the rotation speed at a time point when the short-press has occurred. In the keeping mode, the controller 135a obtains the detection signal from the gyro sensor 135b and determines the rotating direction of the sperm collector 200 according to the inclination angle of the driving device 100.

For example, as illustrated in FIG. 11, the controller 135a rotates the sperm collector 200 in a right direction RC when the inclination direction of the driving device 100 is the right direction R, or rotates the sperm collector 200 in a left direction LC when the inclination direction of the driving device 100 is the left direction L.

The controller 135a shifts to the variable mode when the manual switch 114c is short-pressed in the keeping mode.

<Automatic Switch 114d>

The automatic switch 114d is operated when the power to the motor 131 is turned on or off or when the operating mode (hereinafter, "automatic mode") of the motor 131 is switched.

As described in FIG. 10E, when the automatic switch 114d is long-pressed for two or more seconds, similarly to a case where the manual switch 114c is long-pressed, the power to the motor 131 can be turned on or off.

In the present embodiment, the controller 135a sets the automatic mode when the power is turned on by a long-press on the automatic switch 114d. In the automatic mode, the controller 135a rotates the sperm collector 200 according to predetermined operating contents (a combination of a rotating direction, a rotation speed, and a rotation time) without using the detection signal from the gyro sensor 135b.

In the automatic mode, the controller 135a switches the automatic mode every time the automatic switch 114d is short-pressed. In the present embodiment, as the automatic mode, four types of "P1" to "P4" are defined. The respective automatic modes "P1" to "P4" differ from each other in the combination of the rotating direction, the rotation speed, and the rotation time of the sperm collector 200, and can give different stimulations to a penis inserted in the sperm collector 200.

In the present embodiment, the controller 135a sets the automatic mode "P1" when the power is turned on. The controller 135a sequentially switches the automatic mode "P2", the automatic mode "P3", and the automatic mode "P4" every time the automatic switch 114d is short-pressed, and when the automatic switch 114d is short-pressed in the automatic mode "P4", the controller 135a switches to the automatic mode "P1".

In the automatic mode, because the driving device 100 rotates the sperm collector 200 according to predetermined operating contents, various types of stimulations can be given to a penis without requiring the user to perform any special operation.

<Modification>

Although the driving mechanism DM (negative-pressure introduction-rotation unit) exemplified in the embodiment described above includes the motor 131, the pump 132, the shaft 151, and the bearing unit 137, other configurations may be employed as long as the sperm collector 200 held by the holding unit 120 can be rotated about an axis and the negative pressure can be introduced into the container 202 through the ventilation hole 204c provided in the container 202 of the sperm collector 200.

The holding unit 120 is configured to detachably hold the front portion 204a of the sperm collector 200 (the container main unit 204), but may be configured to detachably hold a region other than the front portion 204a in the container main unit 204.

Although the bearing unit 137 includes the spacer 153 through which the shaft 151 is inserted, the bearing collar 154 arranged in the spacer 153, and the pair of X-rings 155 (155a, 155b) that air-tightly seal a portion between the shaft 151 and the spacer 153 while allowing the shaft 151 to rotate, and the spacer main unit 153a and the pair of X-rings 155 form the pressure regulating space RS, other configurations may be employed as long as the pressure regulating space RS can be formed.

In the embodiment described above, although a configuration of introducing an atmospheric pressure into the pressure regulating space RS by the electromagnetic valve 133 is employed, it is also possible to employ other configurations as long as the negative pressure introduced into the container 202 is reduced. For example, it is possible to employ a configuration in which the pump 132 is controlled to reduce a negative pressure to be generated.

[Summary of Actions and Effects of Aspect Examples of the Present Invention]

<First Aspect>

According to the present aspect, there is provided the driving device 100 that detachably holds the sperm collector 200 and rotates the sperm collector 200 in a state of being held, the sperm collector 200 including the core member 210 that is constituted of an elastic material and has the insertion void 214 for a penis provided therein and the container 202 (the container main unit 204) that is constituted of a hollow member having the opening 204b in a base end and having the ventilation hole 204c in a front portion, and accommodates the core member 210 in an internal space, the driving device 100 including the holding unit 120 that detachably holds the sperm collector 200, and the driving mechanism DM that rotates the sperm collector 200 held by the holding unit 120 about an axis, and introduces a negative pressure into the container 202 via the ventilation hole 204c.

By the driving device 100 according to the present aspect, sperms can be collected efficiently using the sperm collector 200.

<Second Aspect>

In the driving device 100 according to the present aspect, the driving mechanism (negative-pressure introduction-rotation unit) DM includes the motor 131, the pump 132 that generates a negative pressure, the shaft 151 that is rotated by the motor 131 about an axis and communicates between the base end opening 151a provided in one end in an axial direction and the outer peripheral-surface opening 151b provided in an outer peripheral surface by the in-shaft channel 151c, and the bearing unit 137 that rotatably supports the shaft 151 and forms the pressure regulating space RS to which the negative pressure generated by the pump 132 is introduced around the outer peripheral-surface opening 151b, in which the holding unit 120 includes the rotation holder 121 to which a base end portion of the shaft 151 is fixed and that rotates with the shaft 151, and that detachably holds the front portion 204a of the sperm collector 200, and a holder-side packing 122 that communicates between the base end opening 151a of the shaft 151 and the ventilation hole 204c of the sperm collector 200 in an air-tight state when the rotation holder 121 holds the front portion 204a of the sperm collector 200.

In the driving device 100 according to the present aspect, the sperm collector 200 held by the holding unit 120 can be rotated about the axis, and the negative pressure can be introduced into the container 202 of the sperm collector 200 via the ventilation hole 204c with a simple configuration.

<Third Aspect>

In the driving device 100 according to the present aspect, the bearing unit 137 includes a spacer 153 having a cylindrical spacer main unit 153a in which both ends in an axial direction are open and the shaft 151 is inserted and that has the connecting pipes 153b and 153c provided on an outer peripheral surface of the spacer main unit 153a and has an internal channel communicating with an inner void of the spacer main unit 153a, the base-end side X-ring 155a (one end side packing) that is attached to the base end opening 151a of the spacer main unit 153a and air-tightly seals a portion between the shaft 151 and the spacer main unit 153a while allowing the shaft 151 to rotate, and the front-end side X-ring 155b (the other end side packing) that is attached to the front end opening of the spacer main unit 153a and air-tightly seals a portion between the shaft 151 and the spacer main unit 153a while allowing the shaft 151 to rotate, in which the pressure regulating space RS is formed by the spacer main unit 153a, the base-end side X-ring 155a, and the front-end side X-ring 155b, and the pump 132 is connected to the connecting pipe 153b or 153c.

In the driving device 100 according to the present aspect, by introducing a negative pressure to the pressure regulating space RS, the negative pressure can be introduced into the container 202 of the sperm collector 200.

<Fourth Aspect>

In the driving device 100 according to the present aspect, the driving mechanism (the negative-pressure introduction-rotation unit) DM includes the electromagnetic valve 133 that introduces an atmospheric pressure into the pressure regulating space RS when the electromagnetic valve 133 is open.

According to the driving device 100 of the present aspect, by introducing the atmospheric pressure into the pressure regulating space RS, it is possible to decrease a negative pressure to be introduced into the container 202 of the sperm collector 200.

<Fifth Aspect>

The sperm collection system 1 according to the present aspect includes the sperm collector 200 including the core member 210 that is constituted of an elastic material and has the insertion void 214 for a penis provided therein and the container 202 (the container main unit 204) that is constituted of a hollow member having the opening 204b in a base end and having the ventilation hole 204c in a front portion, and accommodates the core member 210 in an internal space, and the driving device 100 including the holding unit 120 that detachably holds the front portion 204a of the sperm collector 200, and the driving mechanism (negative-pressure introduction-rotation unit) DM that rotates the sperm collector 200 held by the holding unit 120 about an axis, and introduces a negative pressure into the container 202 of the sperm collector 200 via the ventilation hole 204c.

According to the sperm collection system 1 of the present aspect, sperms can be collected efficiently.

What is claimed is:

1. A sperm collector driving device that detachably holds a sperm collector and rotates the sperm collector in a state of being held, the sperm collector including a core member that is constituted of an elastic material and has an insertion void for a penis provided therein and a container that is constituted of a hollow member having an opening in one end in an axial direction and having a ventilation hole in an other part in the axial direction, wherein the container accommodates the core member in an internal space thereof, the sperm collector driving device comprising:

a holding unit that detachably holds the sperm collector; and a negative pressure-introduction and rotation unit configured to rotate the sperm collector held by the holding unit about an axis, and introduce a negative pressure into the container via the ventilation hole;

wherein the negative pressure-introduction and rotation unit includes:

a motor, a pump configured to generate the negative pressure, a shaft configured to be rotated by the motor about an axis, wherein a channel within the shaft communicates between one end opening provided in one end of the shaft in the axial direction and an outer peripheral surface opening provided in an outer peripheral surface of the shaft, and a bearing unit that rotatably supports the shaft and forms a pressure regulating space to which the negative pressure generated by the pump is introduced around the outer peripheral-surface opening, and the holding unit includes:

a cup-shaped rotation holder to which the one end of the shaft is fixed, wherein the cup-shaped rotation holder is configured to rotate with the shaft and detachably hold the other part of the sperm collector, and a holder-side packing that is attached on the cup-shaped rotation holder, wherein the holder-side packing communicates between the one end opening of the shaft and the ventilation hole of the sperm collector in an air-tight state when the rotation holder holds the other part of the sperm collector.

2. The sperm collector driving device according to claim 1, wherein the bearing unit includes:

a spacer having a cylindrical spacer main unit which comprises a first end opening at a first end in the axial direction and a second end opening at a second end in the axial direction, wherein the shaft is inserted between the first end opening and the second end opening, and that has a connecting pipe is provided on an outer peripheral surface of the cylindrical spacer main unit, and the connecting pipe has an internal channel communicating with an inner void of the cylindrical spacer main unit, a first end side packing that is attached to the first end opening of the cylindrical spacer main unit and air-tightly seals a portion between the shaft and the cylindrical spacer main unit while permitting the shaft to rotate, and a second end side packing that is attached to the second end opening of the cylindrical spacer main unit and air-tightly seals a portion between the shaft and the cylindrical spacer main unit while permitting the shaft to rotate, and wherein the pressure regulating space is formed by the cylindrical spacer main unit, the first end side packing, and the second end side packing, and the pump is connected to the connecting pipe.

3. The sperm collector driving device according to claim 1, wherein the negative pressure-introduction and rotation unit includes a valve configured to introduce an atmospheric pressure into the pressure regulating space when the valve is open.

4. A sperm collection system comprising:

a sperm collector including a core member that is constituted of an elastic material and has an insertion void for a penis provided therein and a container that is constituted of a hollow member having an opening in one end in an axial direction and having a ventilation hole in an other part in the axial direction, wherein the container accommodates the core member in an internal space thereof; and a sperm collector driving device including a holding unit that detachably holds the sperm collector, and a negative pressure-introduction and rotation unit configured to rotate the sperm collector held by the holding unit about an axis, and introduce a negative pressure into the container via the ventilation hole;

wherein the negative pressure-introduction and rotation unit includes:

a motor, a pump configured to generate the negative pressure, a shaft configured to be rotated by the motor about an axis, wherein a channel within the shaft communicates between one end opening provided in one end of the shaft in the axial direction and an outer peripheral surface opening provided in an outer peripheral surface of the shaft, and a bearing unit that rotatably supports the shaft and forms a pressure regulating space to which the negative pressure generated by the pump is introduced around the outer peripheral-surface opening, and the holding unit includes:

a cup-shaped rotation holder to which one end of the shaft is fixed, wherein the cup-shaped rotation holder is configured to rotate with the shaft and detachably hold the other part of the sperm collector, and a holder-side packing that is attached on the cup-shaped rotation holder, wherein the holder-side packing communicates between the one end opening of the shaft and the ventilation hole of the sperm collector in an air-tight state when the rotation holder holds the other part of the sperm collector.

* * * * *

UNITED STATES PATENT AND TRADEMARK OFFICE
CERTIFICATE OF CORRECTION

| | | |
|---|---|---|
| PATENT NO. | : 12,256,908 B2 | Page 1 of 1 |
| APPLICATION NO. | : 17/303876 | |
| DATED | : March 25, 2025 | |
| INVENTOR(S) | : Kengo Nakamura | |

It is certified that error appears in the above-identified patent and that said Letters Patent is hereby corrected as shown below:

In the Claims

Column 17, Line 29 in Claim 2, Line 8: Please remove the recitation "and that has".

Signed and Sealed this
Tenth Day of June, 2025

Coke Morgan Stewart
*Acting Director of the United States Patent and Trademark Office*